United States Patent [19]

Dyer

[11] Patent Number: 4,629,460
[45] Date of Patent: Dec. 16, 1986

[54] INTRAOCULAR LENS

[76] Inventor: Robert L. Dyer, 4067 Park Blvd., San Diego, Calif. 92103

[21] Appl. No.: 624,196

[22] Filed: Jun. 25, 1984

[51] Int. Cl.⁴ .............................................. A61F 2/16
[52] U.S. Cl. ........................................................ 623/6
[58] Field of Search ................................. 3/13; 623/6

[56] References Cited

U.S. PATENT DOCUMENTS

| 4,174,543 | 11/1979 | Kelman | 3/13 |
| 4,363,143 | 12/1982 | Callahan | 3/13 |
| 4,370,760 | 2/1983 | Kelman | 3/13 |
| 4,403,353 | 9/1983 | Tennant | 3/13 |
| 4,426,741 | 1/1984 | Bittner | 3/13 |
| 4,473,910 | 10/1984 | Grinder | 623/6 |
| 4,476,591 | 10/1984 | Arrott | 623/6 |

OTHER PUBLICATIONS

Copeland Radial (one page drawing).
Cilco Simcoe Lens (four page brochure) (The Simcoe Anterior Chamber Lens-Styles SAC 3 and SAC 5) Mar. 1983.
Coburn Pannu Type II (two page brochure), Coburn Optical Industries, Inc., P.O. Box 2498, Clearwater, FL 33517, Jan. 1984.
Dubroff 044B Intermedics (one page advertisement), p. 55, Intermedics Intraocular, P.O. Box 70670, Pasadena, CA 91107.
Precision–Cosmet's Omnifit II (one page advertisement), 1983.
Kratz/Johnson Laser Iol (one page advertisement), Model PC-35, American Medical Optical, 1402 E. Alton Ave., Irvine, CA 92714.
"Dubroff Anterior Chamber Lens", (Advertisement) Intermedics Intraocular, (Model 044B), P.O. Box 70670, Pasadena, CA 91107, 2 pp., Jan. 1984.

Primary Examiner—Ronald L. Frinks
Attorney, Agent, or Firm—Baker, Maxham & Jester

[57] ABSTRACT

Three radially inwardly curved haptics extend outwardly from equi-distant locations about the periphery of a plano-convex optic. A flat, rounded pod is attached to the distal end of each haptic on the radially outward side thereof.

11 Claims, 3 Drawing Figures

INTRAOCULAR LENS

BACKGROUND OF THE INVENTION

The present invention is related to intraocular lenses for the human eye, and more particularly, to an intraocular lens having a structure that minimizes undesirable movement within the eye and reduces eye irritation.

The replacement of a natural lens with an artificial intraocular lens implant in the human eye is a procedure well known by physicians specializing in ophthalmology. A corneo-scleral incision is made through which the natural lens is removed and the artificial lens inserted. The artificial lens can be affixed in either the anterior or posterior chamber of the eye.

Intraocular lenses of known design and construction typically include a medial light focusing lens through which the patient sees. This lens is referred to as the optic. A support structure is affixed to natural regions of the eye to align and stabilize the optic with respect to the pupil. The support structure, depending upon its construction and location in the eye, can be affixed in position by sutures or by engagement with predetermined eye tissues. Typically, a plurality of arms, loops, struts or feet, collectively referred to as haptics, extend radially outwardly from the optic to provide the required support and stability.

It is desirable that the installation of the intraocular lens be permanent without requiring subsequent surgical adjustments. Any further need for vision correction should be accomplished with eye glasses or other known non-surgical procedures. It is also desirable that the intraocular lens not subject the patient to any discomfort. Furthermore, the intraocular lens should have a durable construction and should resist any type of movement within the eye which will either irritate tissues or degrade the desired correction of vision.

Many intraocular lens designs have been developed heretofore. See for example U.S. Pat. No. 4,174,543. However, prior art intraocular lenses have not provided an optimum design.

SUMMARY OF THE INVENTION

Accordingly, it is the primary object of the present invention to provide an improved intraocular lens.

Another object of the present invention is to provide an intraocular lens design which is universal in size.

Another object of the present invention is to provide an intraocular lens which is resistant to fracture.

Anther object of the present invention is to provide an intraocular lens which minimizes the amount of contact between the haptics and the adjacent eye tissues.

Another object of the present invention is to provide an intraocular lens design which minimizes iris knuckling and chaffing.

Another object of the present invention is to provide an intraocular lens design which resists propellering which can occur where conventional intraocular lenses are too small.

Another object of the present invention is to provide an intraocular lens design which tends to minimize pseudophakokonesis, i.e. a quivering movement of the artificial lens.

Another object of the present invention is to provide an intraocular lens which has self-centering capabilities.

Still another object of the present invention is to provide an intraocular lens design which minimizes pupillary capture.

Finally, another object of the present invention is to provide an intraocular lens which is highly resistant to torquing.

According to the present invention, three radially inwardly curved haptics extend outwardly from equidistant locations about the periphery of a plano-convex optic. A flat, rounded pod is attached to the distal end of each haptic on the radially outward side thereof.

DESCRIPTION OF THE PREFERRED EMBODIMENT

Figure 1:
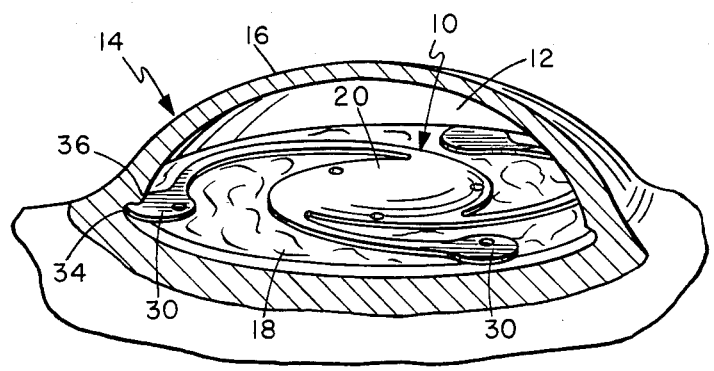
FIG. 1 is a perspective view of a portion of a human eye with portions cut away to show the installation of the intraocular lens of the present invention in the anterior chamber of the eye.
Figure 2:
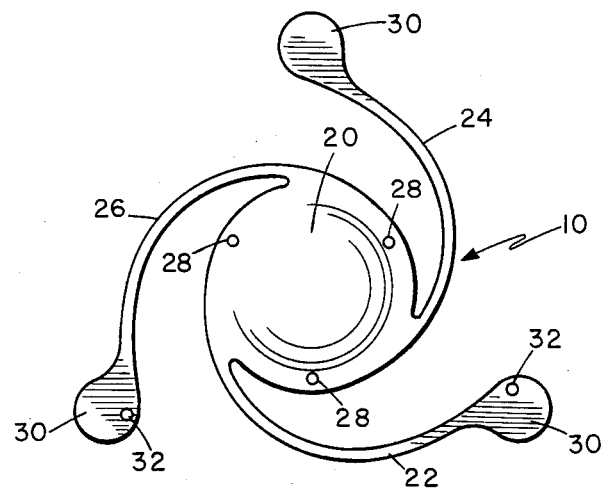
FIG. 2 is a top plan view of the intraocular lens of the present invention.

Referring to FIG. 1, the preferred embodiment 10 of my intraocular lens is shown installed in the anterior chamber 12 of a human eyeball 14. The lens 10 is positioned between the cornea 16 and the iris 18. As illustrated in FIG. 2, the lens 10 includes a plano-convex optic 20 and three radially inwardly curved haptics 22, 24 and 26. The optic is preferably six millimeters in diameter and has three 0.4 millimeter lens manipulating holes 28 spaced equi-distant near the periphery of the optic, between the connection points of the haptics. Surgical instruments may be inserted into these holes during the implanting procedure. The optic 20 may also have a convex-convex shape in lieu of a plano-convex shape.

Figure 3:
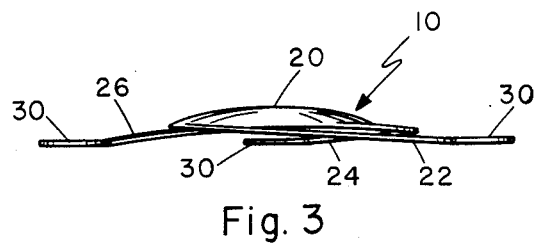
FIG. 3 is a side elevation view of the intraocular lens of the present invention.

As illustrated in FIGS. 2 and 3, each of the curved haptics 22, 24 and 26 extend from the periphery of the optic 20 at locations equi-distant from one another at an approximate angulation of twelve degrees relative to the frontal plane. The frontal plane is the plane which intersects the entire peripheral edge of the optic. The primary radius of curvature of each haptic is approximately twenty degrees greater than the radius of curvature of the outside peripheral edge of the optic. The haptics extend at an acute angle relative to the peripheral edge of the optic. Each haptic has a first portion of uniform cross-section which is preferably ten millimeters in length and 0.25 millimeters in width. It may be desirable that each haptic have a round cross section. Each haptic has a second flared portion connected to the outer end of the first portion.

Attached to the flared second portion of each of the haptics 22, 24 and 26 is a flat, rounded pod 30 preferably measuring 1.5 millimeters in diameter. The overall length of each haptic and pod combination is preferably 13.75 millimeters.

The pods 30 connected to the haptics 22 and 26 each have lens manipulating holes 32 (FIG. 2) near their peripheries, away from the point of contact with the eye tissue. Each of the pods is located on the "outside" of its corresponding haptic, i.e. away from the angle made by the haptic and optic. Stated another way, each pod is attached to the haptic on the radially outward side thereof. As illustrated in FIG. 3, each haptic is vaulted at an approximate ten degree angle at the junction it makes with its corresponding pod along the sagittal plane.

The optic is preferably made of polymethymethacrylate which is a highly inert, synthetic polymer. The haptics, pods and optic of my lens are made of the same material. Such construction is referred to as blended. My intraocular lens could also be made of polymethymethacrylate or polypropylene.

As illustrated in FIG. 1, during the surgical implantation procedure, the optic 20 is positioned over the pupil 10 in the center of the iris 18 in the anterior chamber 12 of the eyeball 14. The optic 20 is thus centered over the pupil by the tripod contact provided by the three haptics and pods. In the case of my lens design, the tripod contact is equi-lateral. Because the points of fixation of my lens form an equi-lateral triangle, there is no tendency towards torquing.

Only a small angular sector of the outer edge of each of the pods 30 contacts the eye tissue at the angle made by the cornea 16 and the iris 18. The outer edge of each pod is received in the circumferentially extending groove 34 between the scleral spur 36 and the iris 18. Preferably, haptic tissue contact is approximately over a thirty-six degree arc. This is very low for intraocular lens designs. When subjected to compression testing, the force necessary to move the end of each haptic of my lens approximately 1.5 millimeters radially inwardly towards the optic is approximately 1.2 grams. Such movement of all three haptics causes the optic to displace forwardly away from the pods (upwardly in FIG. 3) approximately 0.1 millimeters.

The construction of my intraocular lens reduces synechia, i.e. the formation of adhesions between the iris and the intraocular lens, and in particular the haptics.

Having described a preferred embodiment of my invention, it should be apparent that modifications and adaptations thereof will occur to those skilled in the art. Accordingly, the protection afforded by invention should only be limited in accordance with the scope of the following claims.

I claim:

1. An intraocular insert suitable for use as an artificial lens implant in the anterior chamber of a human eye, the anterior chamber having a circumferentially extending groove between the scleral spur and the iris of the eye, the insert comprising:

an optic sized to focus light through the pupil of the eye and having a generally round peripheral edge with a first radius of curvature and defining a frontal plane which intersects the entire peripheral edge of the optic;

three identically shaped haptics integrally formed with and extending at an acute angle from the peripheral edge of the optic at three circumferentially equi-distant spaced locations around the optic, each haptic having an inward second radius of curvature larger than the first radius of curvature and extending at an angle relative to the front plane for overlying the iris when inserted into the eye; and three generally flat, rounded pods, each connected to the distal end of a corresponding one of the haptics and positioned on the radially outward side of the corresponding haptic in a plane generally parallel to the frontal plane so that upon radially inwardly compressing the haptics, the insert can be implanted into the anterior chamber of the eye and the pods will overlie the iris with portions of the outer edges thereof seated in the groove between the scleral spur and the iris to thereby firmly position the optic over the pupil of the eye.

2. An insert according to claim 1 wherein three lens manipulating holes are formed in the periphery of the optic at substantially equi-distant locations.

3. An insert according to claim 1 wherein at least two of the pods have lens manipulating holes formed therein.

4. An insert according to claim 1 wherein each of the haptics extends at an angle of approximately twelve degrees with respect to the frontal plane.

5. An insert according to claim 4 wherein each of the pods extends at an angle approximately ten degrees relative to its corresponding haptis.

6. An insert according to claim 1 wherein the radius of curvature of each haptic is approximately twenty degrees greater than the radius of curvature of the peripheral edge of the optic.

7. An insert according to claim 1 wherein the optic, haptics and pods are integrally formed by polymethymethacrylate.

8. An insert according to claim 1 wherein the optic has a plano-convex configuration.

9. An insert according to claim 1 wherein the configuration of the optic, haptics and pods and the material from which they are formed are such that the distal end of each haptic will move radially inwardly toward the optic approximately 1.5 millimeters in response to a force of approximately 1.2 grams.

10. An insert according to claim 9 wherein the configuration and materials of the insert are such that movement of the distal end of each haptic inwardly toward the optic approximately 1.5 millimeters will cause the optic to be displaced away from its original frontal plane by approximately 0.1 millimeters.

11. An insert according to claim 1 wherein the diameter of each pod is such that it is adapted to contact the groove between the scleral spur and the iris over an arc of approximately thirty-six degrees.

* * * * *